US010548824B2

(12) United States Patent
Nakanishi et al.

(10) Patent No.: US 10,548,824 B2
(45) Date of Patent: Feb. 4, 2020

(54) OXIDATIVE HAIR DYING AND CONDITIONING COMPOSITION AND METHOD FOR BASE BREAKING HAIR WITH AN OXIDATIVE HAIR DYE

(71) Applicant: NUMBER THREE, INC., Chou-ku, Kobe (JP)

(72) Inventors: Kyosuke Nakanishi, Kobe (JP); Ayaka Matsuoka, Kobe (JP)

( * ) Notice: Subject to any disclaimer, the term of this patent is extended or adjusted under 35 U.S.C. 154(b) by 0 days.

(21) Appl. No.: 15/950,049

(22) Filed: Apr. 10, 2018

(65) Prior Publication Data

US 2019/0307663 A1 Oct. 10, 2019

(51) Int. Cl.
*A61K 8/34* (2006.01)
*A61K 8/92* (2006.01)
*A61Q 5/10* (2006.01)

(52) U.S. Cl.
CPC .................. *A61K 8/34* (2013.01); *A61K 8/92* (2013.01); *A61Q 5/10* (2013.01); *A61K 2800/4324* (2013.01); *A61K 2800/882* (2013.01)

(58) Field of Classification Search
CPC ........ A61Q 5/10; A61K 8/411; A61K 8/4926; A61K 8/415; A61K 8/22; A61K 8/342; A61K 8/347; A61K 8/34; A61K 8/922; A61K 8/92; A61K 2800/882; A61K 2800/5426; A61K 2800/596; A61K 2800/5422; A61K 2800/5428; A61K 2800/5424
See application file for complete search history.

(56) References Cited

U.S. PATENT DOCUMENTS

2017/0027832 A1* 2/2017 Wang .................. A61K 8/8147

* cited by examiner

*Primary Examiner* — Eisa B Elhilo
(74) *Attorney, Agent, or Firm* — Elizabeth Yang

(57) ABSTRACT

An oxidative hair dying and conditioning composition and method for base breaking hair with an oxidative hair dye composition provides a hair dying and conditioning composition that consists of a nonionic surfactant having a hydrophilic-lipophilic balance (HLB) of 12 or less, at least one liquid oil agent, at least one alcohol defined by a carbon chain of at least 14 carbon atoms, at least one anion surfactant, at least one amphoteric surfactant, and at least one solvent. Further, a base breaking method helps remove the hair border line by reducing the contrast between a hair's natural base color and highlights through application of a first agent consisting of an oxidative dye and alkaline agent, and a second agent consisting of an oxidative agent that are applied to the hair in two phases separated by a duration of about ten minutes, and rinsing/drying the hair between applications.

4 Claims, 10 Drawing Sheets

800

100

| INGREDIENTS | | | | | |
|---|---|---|---|---|---|
| 102 Nonionic Surfactant | 104 Liquid Oil Agent | 106 Alcohol | 108 Anion Surfactant | 110 Amphoteric Surfactant | 112 Solvent |
| Isostasy glyceryl ether, isostearic acid polyoxyethylene hardened hymic oil, diisostearic acid PEG (6), dioleate PEG (6), PEG-10 glyceryl triisostearate, PEG-15 hydrogenated hydromass oil, diisostearic acid polyglyceryl-3, POE (5), POE (2) Cetyl ether | Vegetable oil, animal oil, wax, petroleum hydrocarbon, higher fatty acid | Myristyl alcohol, cetanol, stearyl alcohol, oleyl alcohol, behenyl alcohol, cetostearyl alcohol | Fatty acid salts, calcium salts, sodium salt and isopropylamino amine salt of fatty acids | Amino acid type amphoteric surfactants and betaine type amphoteric surfactants | Water or a monohydric alcohol such as methanol, ethanol, propanol, benzyl alcohol, phenethyl alcohol, isopropyl alcohol, isobutyl alcohol, hexyl alcohol, 2-ethylhexanol, cyclohexanol, octyl alcohol and butanol |

113

| FIRST AGENT 114a | SECOND AGENT 114b |
|---|---|
| Oxidative Dye<br>Alkaline Agent | Oxidative Agent |

| | | | Example 1 | Example 2 | Example 3 |
|---|---|---|---|---|---|
| Phase | Ingredient Name | HLB | % | % | % |
| A | POLYOXYETHYLENE TRIDECYL ETHER | 8.3 | 10 | | |
| | | 11.4 | | 10 | |
| | | 14.5 | | | 10 |
| B | LAURYL ALCOHOL | / | 6 | 6 | 6 |
| | MYRISTYL ALCOHOL | / | 4 | 4 | 4 |
| C | SODIUM C14-16 OLEFIN SULFONATE | / | 7 | 7 | 7 |
| D | ISOPROPYL ALCOHOL | / | 10 | 10 | 10 |
| Dye | TOLUENE-2,5-DIAMINE | / | 0.2 | 0.2 | 0.2 |
| | 2,4-DIAMINOPHENOXYETHANOL HCl | / | 0.2 | 0.2 | 0.2 |
| Alkaline Agent | ETHANOLAMINE | / | 2 | 2 | 2 |
| Antioxidants | SODIUM SULFITE | / | 0.3 | 0.3 | 0.3 |
| Chelating agent | PENTASODIUM PENTETATE | / | 0.1 | 0.1 | 0.1 |
| Solvent | WATER | / | Up to 100 | Up to 100 | Up to 100 |
| FEEL TEST | | / | ○ | ◎ | ○ |
| STABILITY TEST | | / | ○ | ○ | × |

| FEEL TEST | | | |
|---|---|---|---|
| Evaluation Criteria | ◎ | 26~30 | |
| | ○ | 20~25 | |
| | × | 19 and less | |
| Evaluation Method | MAX Score: 30<br>MIN Score: 10 | Score 3 | (N=10) |
| | | Score 2 | |
| | | Score 1 | |

| Stability Test | | | |
|---|---|---|---|
| Evaluation Criteria | O | | No separation and precipitation |
| | × | | Separation and precipitation |

| | | | Example2 | Example2 | Example3 |
|---|---|---|---|---|---|
| ITEM | INGREDIENT NAME | N of C | % | % | & |
| A | POLYOXYETHYLENE TRIDECYL ETHER TRIDECETH-6 | / | 10 | 10 | 10 |
| B | LAURYL ALCOHOL | 12 | 6 | 6 | 6 |
| | LAURYL ALCOHOL | 12 | 4 | | |
| | MYRISTYL ALCOHOL | 14 | | 4 | |
| | OLEYL ALCOHOL | 16 | | | 4 |
| C | SODIUM C14-16 OLEFIN SULFONATE | / | 7 | 7 | 7 |
| D | ISOPROPYL ALCOHOL | / | 10 | 10 | 10 |
| Dye | TOLUENE-2,5-DIAMINE | / | 0.2 | 0.2 | 0.2 |
| | 2,4-DIAMINOPHENOXYETHANOL HCl | / | 0.2 | 0.2 | 0.2 |
| Alkaline agent | ETHANOLAMINE | / | 2 | 2 | 2 |
| Oxidants | SODIUM SULFITE | / | 0.3 | 0.3 | 0.3 |
| Chelating agent | PENTASODIUM PENTETATE | / | 0.1 | 0.1 | 0.1 |
| Solvent | WATER | / | Up to 100 | Up to 10 | Up to 10 |
| FEEL TEST | | / | × | ◎ | ◎ |
| STABILITY TEST | | / | ○ | ○ | ○ |

| | | | Example 4 | Example 5 | Example 6 | Example 7 |
|---|---|---|---|---|---|---|
| Item | Ingredient Name | SAA | & | % | % | % |
| A | POLYOXYETHYLENE TRIDECYL ETHER TRIDECETH-6 | / | 10 | 10 | 10 | 10 |
| B | LAURYL ALCOHOL | / | 6 | 6 | 6 | 6 |
| | MYRISTYL ALCOHOL | / | 4 | 4 | 4 | 4 |
| C | SODIUM C14-16 OLEFIN SULFONATE | Anionic | 7 | 3.5 | / | / |
| | COCO BETAINE | Amopheteric | / | 3.5 | 7 | / |
| D | ISOPROPYL ALCOHOL | / | 10 | 10 | 10 | 10 |
| Dye | TOLUENE-2,5-DIAMINE | / | 0.2 | 0.2 | 0.2 | 0.2 |
| | 2,4-DIAMINOPHENOXYETHANOL HCl | / | 0.2 | 0.2 | 0.2 | 0.2 |
| Alkaline agent | ETHANOLAMINE | / | 2 | 2 | 2 | 2 |
| Antioxidants | SODIUM SULFITE | / | 0.3 | 0.3 | 0.3 | 0.3 |
| Chelating agent | PENTASODIUM PENTETATE | / | 0.1 | 0.1 | 0.1 | 0.1 |
| Solvent | WATER | / | Up to 100 | Up to 100 | Up to 100 | Up to 100 |
| FEEL TEST | | / | ◎ | ◎ | ◎ | × |
| STABILITY TEST | | / | ○ | ○ | ○ | × |

| | | | Example 7 | Example 8 | Example 9 | Example 10 |
|---|---|---|---|---|---|---|
| ITEM | INGREDIENT NAME | SAA | % | % | % | % |
| A | POLYOXYETHYLENE TRIDECYL ETHER TRIDECETH-6 | / | 10 | 10 | 10 | 10 |
| B | LAURYL ALCOHOL | / | 6 | 6 | 6 | 6 |
| | MYRISTYL ALCOHOL | / | 4 | 4 | 4 | 4 |
| C | SODIUM C14-16 OLEFIN SULFONATE | Anionic | 7 | 3.5 | / | / |
| | COCO BETAINE | Amphoteric | / | 3.5 | 7 | / |
| D | ISOPROPYL ALCOHOL | / | 10 | 10 | 10 | 10 |
| Dye | TOLUENE-2,5-DIAMINE | / | 0.2 | 0.2 | 0.2 | 0.2 |
| | 2,4-DIAMINOPHENOXYETHANOL HCl | / | 0.2 | 0.2 | 0.2 | 0.2 |
| Alkaline agent | ETHANOLAMINE | / | 2 | 2 | 2 | 2 |
| Antioxidant | SODIUM SULFITE | / | 0.3 | 0.3 | 0.3 | 0.3 |
| Chelating agent | PENTASODIUM PENTETATE | / | 0.1 | 0.1 | 0.1 | 0.1 |
| Solvent | WATER | / | Up to 100 | Up to 100 | Up to 100 | Up to 100 |
| FEEL TEST | | / | ◎ | ◎ | ◎ | × |
| STABILITY TEST | | / | ○ | ○ | ○ | × |

| | | | Example 11 | Example 12 | Example 13 | Example 14 |
|---|---|---|---|---|---|---|
| ITEM | INGREDIENT NAME | | % | % | % | % |
| A | POLYOXYETHYLENE TRIDECYL ETHER TRIDECETH-6 | / | 10 | 10 | 10 | 10 |
| B | LAURYL ALCOHOL | / | 6 | 6 | 6 | 6 |
| | MYRISTYL ALCOHOL | / | 4 | 4 | 4 | 4 |
| C | SODIUM C14-16 OLEFIN SULFONATE | / | 7 | 7 | 7 | 7 |
| D | ISOPROPYL ALCOHOL | / | 10 | 7 | 3.5 | 0 |
| Dye | TOLUENE-2,5-DIAMINE | / | 0.2 | 0.2 | 0.2 | 0.2 |
| | 2,4-DIAMINOPHENOXYETHANOL HCl | / | 0.2 | 0.2 | 0.2 | 0.2 |
| Alkaline agent | ETHANOLAMINE | / | 2 | 2 | 2 | 2 |
| Antioxidants | SODIUM SULFITE | / | 0.3 | 0.3 | 0.3 | 0.3 |
| Chelating agent | PENTASODIUM PENTETATE | / | 0.1 | 0.1 | 0.1 | 0.1 |
| Solvent | WATER | / | Up to 100 | Up to 100 | Up to 100 | Up to 100 |
| FEEL TEST | | / | 27◎ | 27◎ | 27◎ | 27◎ |
| STABILITY TEST | | / | ○ | ×(Semi-solid) | ×(Semi-solid) | ×(Semi-solid) |

Decolorization is sufficient for 10 minutes after application, whereas coloration is insufficient for 10 minutes, and the coloration is blue → green → It is preferable to use a color that produces a blue color and does not produce a red color because it is colored in the order of yellow → orange → red → purple.

OXIDATIVE HAIR DYING AND CONDITIONING COMPOSITION AND METHOD FOR BASE BREAKING HAIR WITH AN OXIDATIVE HAIR DYE

FIELD OF THE INVENTION

The present invention relates generally to an oxidative hair dying and conditioning composition and method for base breaking hair with an oxidative hair dye composition. More so, the present invention relates to a hair dying and conditioning composition that consists of a nonionic surfactant having a hydrophilic-lipophilic balance (HLB) of 12 or less, at least one liquid oil agent, at least one alcohol defined by a carbon chain of at least 14 carbon atoms, at least one anion surfactant, at least one amphoteric surfactant, and at least one solvent; and whereby a base breaking method helps remove the hair border line by reducing the contrast between a hair's natural base color and highlights through application of a first agent consisting of an oxidative dye and alkaline agent, and a second agent consisting of an oxidative agent that are applied to the hair in two phases separated by a duration of about ten minutes, and rinsing/drying the hair between applications.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

It is known in the field of hair care that the coloring, or dying, of human hair is a popular technique to change a person's look, style, and fashion. However, due to the inherent composition of hair fiber, and the chemical and mechanical exposure encountered by the hair fibers during normal care and styling, obtaining and maintaining a precise color can be problematic and imperfect. Typically, liquid compositions containing dyes, fragrances, and oils are used to dye human hair are applied directly to the hair by, for example, squeezing dye liquid through a nozzle, or spraying a dye composition, or applying the dye by any other conventional method. Often hair dyeing involves first applying a dye composition and then fixing it by an oxidation step using peroxide or the like.

It is also known that temporary hair dyes last through a few shampooings, while semi-permanent hair colors are retained for three to six weeks of shampooings. The permanent dyes or colors, which are often equally employable on plant derived and synthetic fibers, as well as hair keratin, cannot be shampooed out from hair fibers. In virtually all prior art, using permanent hair dyes requires hydrogen peroxide along with the particular dyestuffs. During the application, the mixture enters into the hair fibers and reacts therein to form larger dyes of a predetermined color. Since the dye molecules formed are larger than the molecules entering the hair fibers, the formed dyes are trapped within the hair fibers, and are unable to diffuse out of the fibers. Consequently, the resulting coloring is trapped within the hair fiber and is permanent.

Generally, oxidation hair dyeing agents are widely used because they have efficacious dyeability and high durability. The oxidation hair coloring agent comprises a first agent containing an oxidation dye and an alkaline agent and a second agent containing an oxidizing agent. This dye can be used by mixing the agents at the time of use. When this is applied to the hair, the alkaline agent expands the hair to increase the penetrability of the oxidation dye and reacts with the oxidizing agent (usually hydrogen peroxide), whereby coloring of the oxidation dye and melanin in the hair causing hair to be dyed.

Unfortunately, hair dyeing with oxidative hair dye generally causes roughness of the cuticle of the hair, which causes worsening of the touch (comb) of the hair. Especially when the object to be dyed contains gray hair, the difference between the newly extending white portion and the dyed black portion is conspicuous, so it is necessary to frequently dye hair, so this problem is more pronounced become.

Often in the case of hair including gray hair, the gray hair has a hydrophobic nature, and hence it is said that it is difficult for penetration of oxidation dye and it is difficult to stain. Heretofore, Japanese patent JP-A-2009-161492 teaches a first agent for oxidation hair dye in which a specific surfactant and a specific ester are combined in combination to solve these problems.

Conventionally, oxidative hair coloring agents have good hair dyeing properties, whereas scalp and the like have irritation have been regarded as disadvantages. Also, with the recent trend of hair color, it has become desired to increase the brightness of the hair to brighten the hair. However, to brighten and dye the hair, it is necessary to increase the amount of the alkaline agent contained in the first agent in two-part oxidation hair dye. Also, when ammonia sufficient for dyeing is contained, irritating odors are conspicuous, and further there are cases where irritation to the scalp is observed in many cases, and it is well known to put a burden on hair. Several hair bleaching agents and oxidation hair dyes to solve these problems have been proposed, which have little irritation odor, low irritation to the scalp, and little burden on the hair.

Another hair dye Japanese patent JP-A-10-25230 teaches a method in which the amount of ammonia in the first hair dying agent is reduced and another alkaline agent is used in combination in the two-agent oxidation hair dye. However, with this method, hair cannot be dyed in a sufficiently bright coloration, and when used in a large amount, there is a problem that it is highly persistent in the scalp and stimulation is easily given to the scalp.

Further, Japanese patent JP-A-2001-354531 that the amount of ammonia in the first agent is 1% by weight or less, the amount of the organic amine is 0.1 to 5% by weight, and the total amount of the first agent and the second agent Two-agent type oxidation hair dyeing agents or hair bleaching agents having a content of an anionic surfactant in the composition of 5 to 60% by weight and a content of water of 25 to 70% by weight have also been proposed. According to this, the hair is dyed in a light hue, and an oxidation hair dye or a hair bleaching agent having a low irritating odor and a low irritation to the scalp is provided. However, organic amines have less irritating odor compared to ammonia, but they have high persistence to the scalp and may cause hair damage and skin irritation. Furthermore, this oxidation hair dye or hair bleaching agent is in a liquid state, inferior in handleability when applied to hair, and has a problem that it diffuses and permeates easily when adhering to the scalp.

Japanese patent JP-A-2004-339179 teaches that the following oxidation hair coloring agents have been proposed, in which an amount of an alkaline agent such as an ammonia in the first agent is reduced, an organic amine is used together with an oxidizing dye, an oxidizing agent, and anionic surfactant of 100000 cps. However, organic amines have a less irritating odor compared to ammonia, but they are more likely to remain on the scalp and cause hair damage and skin irritation. In addition, this oxidative hair dye or hair depigmenting agent is in a liquid state, which is inferior in handleability when applied to hair, and has the problem of spreading and penetrating when attached to the scalp.

Furthermore, Japanese patent JP-A-2004-26699 teaches that an oxidation hair coloring agent has been proposed which is characterized in that the amount of alkaline agent such as ammonia in the first agent is reduced and combined with monoethanolamine hydrochloride and the pH is 8 to 12. However, there was little irritant odor and low stimulus to the scalp, but the burden on the hair was not satisfactory.

Specifically, it is necessary to provide an oxidative hair dying and conditioning composition that is stable over time. The stability helps overcome adverse effects of dying hair, such as roughness of the hair cuticle, and the undesirable/rough feel of the hair to finish is reduced to a lesser degree.

Damage to the hair is caused by the surface cuticle being peeled off and the internal moisture flowing out. Particularly during shampooing, the cuticle is in a state susceptible to friction, which is a major factor of damage to the hair. For that reason, shampoo for damaged hair is required to protect the cuticle and reduce friction. Silicone, a synthetic raw material commonly used for shampoo for damage hair, coats the surface of hair and plays a role of reducing the friction of the cuticle. Silicone, a synthetic raw material that is generally used in shampoos for damaged hair, generally serves to reduce the friction of the hair cuticle by coating the hair surface. It can be said that it is a highly effective raw material to achieve smooth fingering and to prevent damage to hair.

Thus, because of the high adhesion of hair to hair, highly polymerized silicone*1 and modified silicone*2 blended into hair care products, using this product for a long period of time may result in a phenomenon called "build-up" that clogs hair follicles on the scalp and accumulates excessively on the hair surface. As a result, it may adversely affect the scalp and hair, such as deterioration of the scalp environment and peeling of the hair cuticle. In addition, it may interfere with hair color staining and perming.

*1 Highly polymerized silicone is applied to the hair as waterproof, moisturizing and sebum resistant as a silicone for protective coatings.

*2 Modified Silicone has better adsorption than high-polymerized silicone and improves the durability of the conditioning effect.

In recent years, the market size of non-silicone cosmetics has been expanding due to the increase in the natural needs of the cosmetics market as a consumer needs that devalue silicone. Since non-silicon shampoo does not use silicone literally, there is no adverse effect on hair surface and scalp by build-up. However, since there is no raw material that can substitute for silicone (adhesion with sustainability, smoothness to hair), non-silicon shampoo has weak function to suppress the friction of hair during shampooing, it is unsuitable.

As described above, it is difficult to combine damage care due to the friction reducing effect at the time of shampooing and scalp care for keeping the scalp and hair normal without preventing build-up in the development of shampoo for damaged hair, so it is technically a trade-off relationship. In case from these backgrounds, the need for non-silicone is also increasing in the development of oxidative hair coloring agents.

Recently, "Ammonium-free", which does not use ammonia as an oxidative hair coloring agent with a low irritation odor, low irritation to the scalp, and a low burden on hair, has been strongly desired. In addition, synthetic hair dyes, such as PPD, p-phenylene diamine are used in many of the commercially available white hair dyes and hair coloring agents for white hair dyeing. Because PPD can easily produce various color tones and can be dyed with a deep color, it is especially essential for white hair dyeing and hair coloring agents, but it is known to be a component that causes symptoms of allergies It is.

Recently, "PPD-free" has come to be strongly desired. Furthermore, more reliable and safer products are required, in the case of oxidative hair dyes, not only the products of "Silicon-free", "Ammonia-free", and "PPD-free", but also the products of autographically certified COSMOS and VEGAN and HALAL are becoming more desirable. Also, as much as possible, the tendency to adopt renewable and sustainable natural raw materials has increased. As well as its components, it is becoming more and more necessary to consider the environment to its own factory sites, manufacturing processes, and packaging that have received two certifications, COSMOS and ISO22716.

Other proposals have involved dying hair. The problem with these hair dye compositions is that they do not include surfactants that also help to condition hair, and leave hair smooth with soft cuticles. Also, the dye compositions are not always stable or healthful for the hair. Even though the above cited hair dye compositions meet some of the needs of the market, a hair dying and conditioning composition that consists of a nonionic surfactant having a hydrophilic-lipophilic balance (HLB) of 12 or less, at least one liquid oil agent, at least one alcohol defined by a carbon chain of at least 14 carbon atoms, at least one anion surfactant, at least one amphoteric surfactant, and at least one solvent; and that is also effective for base breaking hair in phases, is still desired.

SUMMARY

Illustrative embodiments of the disclosure are generally directed to an oxidative hair dying and conditioning composition and method for base breaking hair with an oxidative hair dye composition. The oxidative hair dye composition is configured to colorize and condition hair fibers, so as to create a superior finished texture with reduced adverse effects associated with dying of hair, such as roughness of the cuticle. The hair dye composition is also a stable composition that works well with hair follicles to create an enhanced finishing look and feel of the hair.

In some embodiments, the oxidative hair dye composition consists of: a nonionic surfactant having a hydrophilic-lipophilic balance (HLB) of 12 or less, at least one liquid oil agent, at least one alcohol defined by a carbon chain of at least 14 carbon atoms, at least one anion surfactant, at least one amphoteric surfactant, and at least one solvent.

The base breaking method is effective for removing a hair border line by reducing the contrast between a hair's natural base color and highlights. The method involves application of a first agent consisting of an oxidative dye and alkaline agent, and a second agent consisting of an oxidative agent that are applied in different two phases separated by a duration of about ten minutes between applications, and washing and drying of the hair.

In another aspect, the nonionic surfactant is about 12% to 18% by weight of the total composition.

In another aspect, the liquid oil agent is about 5% to 15% by weight of the total composition.

In another aspect, the liquid oil agent is about 7.5% to 11.5% by weight of the total composition.

In another aspect, the alcohol is about 0.001% to 5% by weight of the total composition.

In yet another aspect, the alcohol is about 0.01% to 3% by weight of the total composition.

In yet another aspect, the anion surfactant is about 3% to 12% by weight of the total composition.

In yet another aspect, the amphoteric surfactant is about 3% to 12% by weight of the total composition.

In yet another aspect, the anion surfactant is about 6% to 9% by weight of the total composition.

In yet another aspect, the amphoteric surfactant is about 6% to 9% by weight of the total composition.

In yet another aspect, the solvent is about 5% to 25% by weight of the total composition.

In yet another aspect, the solvent is about 10% to 20% by weight of the total composition.

One objective of the present invention is to provide an oxidative hair dying and conditioning composition for colorizing and conditioning hair fibers.

Another objective is to provide a stable oxidative hair dying and conditioning composition that remains stable over time.

Yet another objective is to provide an oxidative hair dying and conditioning composition that enhances the feel of finished hair while reducing the roughness of the cuticle.

Yet another objective is to improve the stability of the oxidative hair dying and conditioning composition.

Yet another objective is to prevent the hair from drooping down while the oxidative hair dying and conditioning composition is being applied.

Yet another objective is to cover gray or white hair.

Yet another objective is to change to a color regarded as more fashionable or desirable.

Yet another objective is to restore the original hair color after it has been discolored by hairdressing processes or sun bleaching.

Yet another objective is to provide a unique method for base breaking hair, so as to remove a hair border line.

Yet another objective is to provide a sulfate-free oxidative hair dying and conditioning composition.

Yet another objective is to provide an easy to apply oxidative hair dying and conditioning composition.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which:

FIG. 1 illustrates a Table illustrating a list of ingredients for an exemplary oxidative hair dying and conditioning composition, in accordance with an embodiment of the present invention;

FIGS. 2A-2C illustrate a Table referencing one exemplary embodiment of an oxidative hair dying and conditioning composition and treatment results, where FIG. 2A lists ingredients for the composition, FIG. 2B illustrates a Table referencing hair softness evaluation criteria, and FIG. 2C illustrates a Table referencing stability criteria for the composition, in accordance with an embodiment of the present invention;

FIG. 3 illustrate a Table referencing a second embodiment of an oxidative hair dying and conditioning composition and treatment results, listing the ingredients for the composition, in accordance with an embodiment of the present invention;

FIG. 4 illustrate a Table referencing a third embodiment of an oxidative hair dying and conditioning composition and treatment results, listing the ingredients for the composition, in accordance with an embodiment of the present invention;

FIG. 5 illustrate a Table referencing a fourth embodiment of an oxidative hair dying and conditioning composition and treatment results, listing the ingredients for the composition, in accordance with an embodiment of the present invention;

FIG. 6 illustrate a Table referencing a fifth embodiment of an oxidative hair dying and conditioning composition and treatment results, listing the ingredients for the composition, in accordance with an embodiment of the present invention;

FIG. 8A shows the hair parted, FIG. 8B shows a first agent applied to the hair, FIG. 8C shows the hair after the first rinsing and drying, FIG. 8D shows a second agent applied to the hair, and FIG. 8E shows the hair after the second rinsing and drying with the color differences between the root portion and upper portion of the hair follicles reduced, in accordance with an embodiment of the present invention;

Like reference numerals refer to like parts throughout the various views of the drawings.

DETAILED DESCRIPTION OF THE INVENTION

Figure 7:
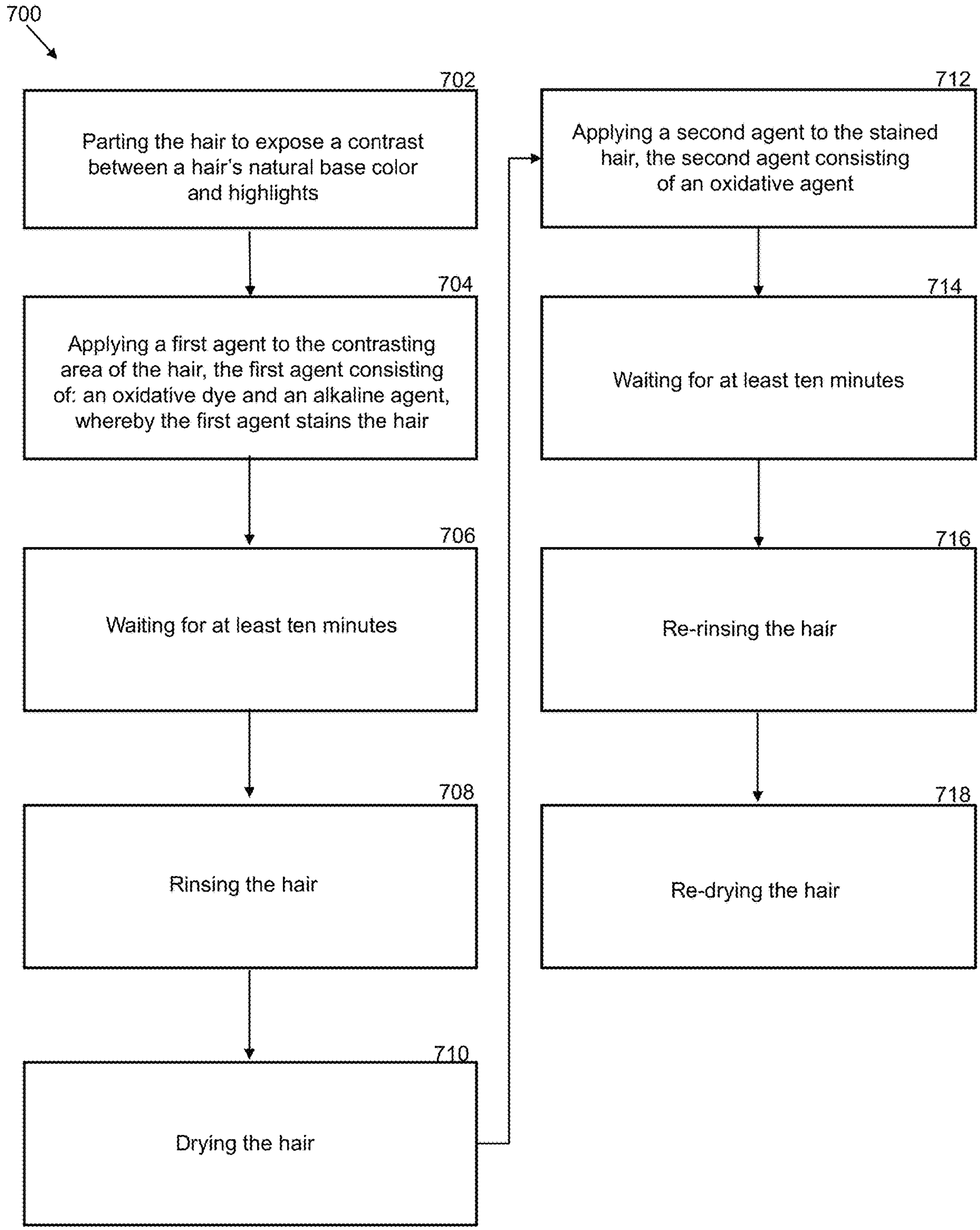
FIG. 7 illustrates a flowchart of an exemplary method for base breaking hair with an oxidative hair dye composition, in accordance with an embodiment of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

An oxidative hair dying and conditioning composition 100 and method 700 for base breaking hair with an oxidative hair dye composition is referenced in FIGS. 1-10. The oxidative hair dye composition 100 is configured to colorize and condition hair fibers. The composition 100 creates a superior finished texture with reduced adverse effects associated with dying of hair, such as roughness of the cuticle. The composition 100 also works to stabilize the hair for an enhanced finishing look and feel of the hair.

As the Table in FIG. 1 references, the oxidative hair dye composition 100 consists of: a nonionic surfactant 102 having a hydrophilic-lipophilic balance (HLB) of 12 or less, at least one liquid oil agent 104, at least one alcohol 106 defined by a carbon chain of at least 14 carbon atoms, at least one anion surfactant 108, at least one amphoteric surfactant 110, and at least one solvent 112. The surfactants, oils, alcohols, and other ingredients can be combined in various combinations and percent by total weights.

In one non-limiting embodiment, the nonionic surfactant 102 is about 12% to 18% by weight of the total composition. Though in other embodiments, other weights of total composition may be used in the composition 100. For the present invention, the surfactants that are used are not particularly limited as long as they can be adopted as an oxidation hair dye that are known and widely adopted. Exemplary surfactants include: anion, amphoteric surfactant, nonionic surfactant, and cationic surfactant.

Among the surfactants, the nonionic surfactant and cationic surfactants are preferable from the viewpoint that they can be dyed more uniformly and densely, and nonionic surfactants are more preferable. From the viewpoint of further reducing the adverse effect on the feel of hair, anion, amphoteric surfactant 1, nonionic surfactant 102 and the like are preferable, and nonionic surfactant 102 in combination with anionic surfactants, and/or nonionic surfactant 102 in combination with amphoteric surfactant 110 are more preferred.

Therefore, from the viewpoint that the dyeing can be more uniformly darkened and the adverse effect on the feel of the hair can be further reduced, at least one nonionic surfactant 102 and at least one anion, amphoteric. Further, from the viewpoint that the effect of the present invention can be exhibited more effectively, the oxidation hair dye of the present invention contains, as a surfactant, at least one nonionic surfactant 102 having HLB of 12 or less, preferably one kind of anion and amphoteric surfactant 110 in combination, more preferably at least one kind of anion and/or at least one kind of amphoteric surfactant 110, more preferably each containing a specific content.

Exemplary nonionic surfactants 102 having a hydrophilic-lipophilic balance (HLB) of 12 or less may include, without limitation: isostasy glyceryl ether (HLB value 5), isostearic acid polyoxyethylene hardened hymic oil (HLB value 5), diisostearic acid PEG (6) (HLB5), dioleate PEG (6) (HLB value 5), PEG-10 glyceryl triisostearate (HLB value 5), PEG-15 hydrogenated hydromass oil (HLB value 5), diisostearic acid polyglyceryl-3 (HLB value 5), POE (5), POE (2) Cetyl ether (HLB value 5), PEG-3 glyceryl isostearate (HLB value 6) and diisostearic acid PEG-, Triisostearate POE (20) hydrogenated flax oil (HLB value 6), POE (3) Cetyl ether (HLB value 6), POE (7) Hydrogenated flax oil (HLB value 6), Isostearic acid POE (15) Hydrogenated flax oil (HLB value 7), Diisostearate POE), Glyceryl (HLB value 7), pyruvic acid POE (6) (HLB value 7), sorbitan sesquistearate (HLB value 7), TPO (30) hydrogenated hydrated oil (HLB value 7), isostearic acid POE (HLB value 7), isostearic acid POE (5) glyceryl (HLB value 8), isostearic acid POE (20) hydrogenated flax oil (HLB value 8), diisostearic acid POE (12) POE (20) glyceryl (HLB value 8), POE (5) isostearyl ether (HLB value 8), POE (5) (HLB value 8), isostearic acid PEG-30 hydrogenated flax oil (HLB value 9), isostearic acid POE (6) (HLB value 9), hydrogenated lecithin (HLB value 9), isostearic acid POE (10) glyceryl (HLB value 10), isostearic acid POE (8) glyceryl (HLB value 10), diisostearic acid POE (20) glyceryl (HLB value 10), triisostearate POE (30) glyceryl (HLB value 10) (HLB value 10), POE (7) Cetyl ether (HLB value 10), POE (8) (HLB value 10) monoisostearic acid POE (10) isostearyl ether (HLB value 11), Isostearic acid POE (10) (HLB value 11), Isostearic acid POE (15) glyceryl (HLB value of 12), POE (15) isostearyl ether (HLB value 12), and the like.

Other exemplary nonionic surfactants 102 having a hydrophilic-lipophilic balance (HLB) of 12 or less may include, Polyoxyethylene monoalkyl ether lauromacrogol (HLB value 13.6), Polyoxyethylene lauryl ether (HLB value: 9.7), Polyoxyethylene cetyl ether (HLB value 5.3, 11.2, 11.9), Polyoxyethylene lauryl ether (HLB value: 9.7), Polyoxyethylene cetyl ether (HLB value 5.3, 11.2, 11.9), Polyoxyethylene oleyl ether (HLB value 4.9, 9.0), Polyoxyethylene stearyl ether (HLB value 4.9, 10.7), Polyoxyethylene alkyl (12-14) ether (HLB value 8.1), Polyoxyethylene tridecyl ether (HLB value 8.3, 11.4), Polyoxyethylene myristyl ether (HLB value 7.6, 9.0), Polyoxyethylene isostearyl ether (HLB value: 4.9. 9.0), Polyethylene glycol dilaurate (HLB value: 9.7), Polyethylene glycol 150 dipalmitate 150 (HLB value 3.6), Polyethylene glycol dioleate (HLB value: 8.0), Polyethylene glycol distearate (1) (HLB value 8), Polyethylene glycol diisostearate (HLB value 8.0, 10.3), Polyoxyethylene glyceryl isostearate (HLB value 10.2), Polyoxyethylene glyceryl triisostearate (HLB value 7.2, 10.2), Yet additional nonionic surfactants 102 having a hydrophilic-lipophilic balance (HLB) of 12 or less may include, Polyoxyethylene trimethylolpropane (HLB value: 6.5) Distearate Polyoxyethylene sorbitan (6 E.O.) monooleate (HLB value: 11.8), Polyoxyethylene sorbitan lambda trioleate (20 EO) (HLB value: 10.8), Polyoxyethylene sorbitan (20 EO) (HLB value: 10.7), Tristearate polyoxyethylene hardened castor oil 20 (HLB value 10.1), Polyoxyethylene hardened castor oil (HLB value 10.1), Lauric acid polyoxyethylene hydrogenated castor oil (HLB value 9), Monoisostearic acid polyoxyethylene hydrogenated castor oil (HLB value 8.6, 12.0), Lambda tetraoleate polyoxyethylene sorbit (HLB value 5.0, 11.2), Lambda pentaoleate polyoxyethylene sorbit (HLB value 11.4), Lambda isostearate polyoxyethylene sorbit (3 E.O.) (HLB value: 4.7) and the like. The nonionic surfactant 102*s* having a hydrophilic-lipophilic balance (HLB) of 12 or less may be used singly or in combination of two or more.

In one non-limiting embodiment, the liquid oil agent 104 used in the composition 100 is about 5% to 15% by weight of the total composition. In another embodiment, the liquid oil agent 104 is about 7.5% to 11.5% by weight of the total composition. Though in other embodiments, other percentages of weight of total composition may be used in the composition 100. Liquid oil agent 104 may be used singly or in combination of two or more. The oily component of the liquid and solid fat and oil agent is a liquid and a solid oil, for example, a higher alcohol (i.e. myristyl alcohol) having C 12 or more.

The oily component of the liquid and solid fat and oil agent is not particularly limited, but examples thereof include vegetable oil, animal oil, wax, petroleum hydrocarbon, higher fatty acid, and higher alcohol. Among these, higher alcohols having C 14 or higher are preferable from the viewpoint that the effect of the present invention can be exhibited more reliably.

Examples of higher alcohols having 12 to 25 carbon atoms may include, without limitation: myristyl alcohol, cetanol, stearyl alcohol, oleyl alcohol, behenyl alcohol, cetostearyl alcohol and the like. Examples of the higher fatty acid include lauric acid, myristic acid, palmitic acid, stearic acid, behenic acid, oleic acid, isostearic acid, 12-hydroxystearic acid, and undecylenic acid.

Examples of vegetable oils may include, without limitation: include avocado oil, almond oil, olive oil, sesame oil, rice bran oil, safflower oil, soybean oil, corn oil, rapeseed oil, palm oil, castor oil, grape seed oil, coconut oil and hydrogenated oil etc., Examples of animal oils include emu oil, horse oil, mink oil and the like. Examples of waxes include jojoba oil, carnauba wax, candelilla wax, rice bran wax, lanolin and shellac.

Examples of petroleum hydrocarbons may include, without limitation: light isoparaffin, light liquid isoparaffin, squalane, paraffin, liquid paraffin, liquid isoparaffin, petrolatum and microcrystalline wax etc., Examples of the silicone include dimethyl silicone, cyclic silicone, polyether-modified silicone, amino-modified silicone, polyglycerin-modified silicone, and methylphenyl silicone.

In one non-limiting embodiment, the alcohol 106 used in the composition 100 is about 0.001% to 5% by weight of the total composition. In another embodiment, the alcohol 106 is about 0.01% to 3% by weight of the total composition. Though in other embodiments, other weights of total composition for the alcohol 106 may be used in the composition 100. The higher alcohol 106 having C12 or more may be used singly or in combination of two or more.

In one non-limiting embodiment, the anion surfactant 108 used in the composition 100 is about 3% to 12% by weight of the total composition. In another embodiment, the anion surfactant 108 is about 6% to 9% by weight of the total composition. Though in other embodiments, other weights of total composition may be used in the composition 100. The anion surfactant 108 may be used singly or in combination of two or more.

Examples of the anionic surfactant 108 may include, without limitation: fatty acid salts such as calcium salts, sodium salt and isopropylamino amine salt of fatty acids such as coconut oil fatty acid, lauric acid, miristinic acid, palmitic acid, stearic acid and oleic acid etc.), Allyl ether carboxylate (Such as polyoxyethylene lauryl ether acetate, polyoxyethylene lauryl ether acetate, sodium lauryl ether acetate etc).

Other examples of the anionic surfactant 108 may include, without limitation: Acyl lactate (such as stearoyl lactylate, isostearyl lactate etc.,) N-acyl sarcosine salts (such as coconut oil fatty acid sarcosine, coconut oil fatty acid sarcosine sodium, lauroyl sarcosine, lauroyl sarcosinate sodium, etc.), N-acyl glutamic acid salt (coconut oil fatty acid acyl glutamic acid potassium salt, coconut oil fatty acid acyl glutamic acid sodium salt, lauroyl glutamic acid, potassium lauroyl glutamate, sodium lauroyl glutamate, lauroyl glutamic acid, sodium lauroyl glutamate, potassium lauroyl glutamate, stearoyl glutamic acid, stearoyl glutamate, stearoyl Potassium glutamate, sodium N-acyl-L-glutamate, sodium N-lauroyl-L-glutamate).

Other examples of the anionic surfactant 108 may include, without limitation: N-acylmethylalanine salt (coconut oil fatty acid methyl alanine, coconut oil fatty acid methyl alanine sodium, lauroyl methyl alanine, lauroyl methyl alanine sodium, myristoyl methyl alanine, myristoyl methyl alanine sodium, etc.), N-acyl methyl taurine salt (coconut oil fatty acid methyl taurine potassium, coconut oil fatty acid methyl taurine sodium, coconut oil fatty acid methyl taurine potassium magnesium, lauroyl methyl taurine sodium, myristoyl methyl taurine sodium).

Other examples of the anionic surfactant may include, without limitation: Alkanesulfonates (such as sodium alkanesulfonate), alkylsulfosuccinates [sodium di (2-ethylhexyl) sulfosuccinate, disodium lauryl sulfosuccinate and the like, Acyl isethionate (such as coconut oil fatty acid ethyl ester sodium sulfonate), Alkyl sulfate ester salts (sodium alkyl sulfate, sodium lauryl sulfate, potassium lauryl sulfate, magnesium lauryl sulfate, etc.), Alkyl ether sulfuric acid ester salt (sodium polyoxyethylene alkyl ether sulfate, sodium polyoxyethylene lauryl ether sulfate, etc.), Monoalkyl phosphate ester salts (lauryl phosphate, sodium lauryl phosphate, etc.), Polyoxyethylene alkyl ether phosphate ester salts (polyoxyethylene lauryl ether phosphate, sodium polyoxyethylene lauryl ether phosphate, polyoxyethylene cetyl ether phosphate, sodium polyoxyethylene cetyl ether phosphate, polyoxyethylene stearyl ether phosphate Acid, polyoxyethylene stearyl ether phosphate sodium, polyoxyethylene oleyl ether phosphate, sodium polyoxyethylene oleyl ether phosphate, etc.), and the like. Among these, sodium polyoxyethylene alkyl ether sulfate is preferable, and polyoxyethylene (number of moles of added ethylene oxide: 2 to 6, preferably 2 to 4) alkyl (number of carbon atoms: 5 to 20, preferably 8 to 16, more preferably 10 to 14) sodium ether sulfate.

In one non-limiting embodiment, the amphoteric surfactant 110 used in the composition 100 is about 3% to 12% by weight of the total composition. In another embodiment, the amphoteric surfactant 110 is about 6% to 9% by weight of the total composition. Though in other embodiments, other weights of total composition for the amphoteric surfactant 110 may be used in the composition 100. The amphoteric surfactant 110 may be used singly or in combination of two or more.

Examples of an amphoteric surfactant 110 may include, without limitation: amino acid type amphoteric surfactants and betaine type amphoteric surfactants. Furthermore, specific examples of the amino acid type amphoteric surfactant include: Glycine type amphoteric surfactant such as 2-alkyl-N-carboxymethyl-N-hydroxyethyl imidazolinium betaine, undecyl hydroxyethyl imidazolinium betaine sodium, alkyl diaminoethyl glycine hydrochloride, N-coconut oil fatty acid acyl-N'-carboxyethyl-N'-Coconut oil fatty acid acyl-N'-carboxyethoxyethyl-N'-carboxyethylethylenediamine disodium, N-coconut oil fatty acid acyl-N'-carboxymethoxyethyl-N'-carboxymethylethylenediamine disodium, Sodium lauryl diamino ethyl glycine etc.; Aminopropionic acid type amphoteric surfactant such as Sodium laurylaminopropionate and sodium laurylaminodipropionate and like.

Further, specific examples of the betaine type amphoteric surfactant include aminopropyl betaine type amphoteric surfactants such as Coconut oil alkylbetaine, lauryldimethylaminoacetic acid betaine, stearyldimethylaminoacetic acid betaine, stearyl dimethyl betaine sodium, coconut oil fatty acid amidopropyl betaine, palm oil fatty acid amidopropyl betaine and lauric acid amidopropyl betaine; Sulfobetaine type amphoteric surfactant such as Lauryl hydroxysulfobetaine and like.

In one non-limiting embodiment, the solvent 112 used in the composition 100 is about 5% to 25% by weight of the total composition. In another embodiment, the solvent 112 is about 10% to 20% by weight of the total composition. Though in other embodiments, other weights of total composition for the solvent 112 may be used in the composition 100. The solvent 112 may be used singly or in combination of two or more.

In some embodiments, the solvent 112 may include, without limitation, at least one or two selected from the following: water or a monohydric alcohol such as methanol, ethanol, propanol, benzyl alcohol, phenethyl alcohol, isopropyl alcohol, isobutyl alcohol, hexyl alcohol, 2-ethylhexanol, cyclohexanol, octyl alcohol and butanol, pentanol, Ketones such as acetone and methyl ethyl ketone; Lower alcohols such as ethanol, 2-propanol(isopropyl alcohol), butanol, isopropyl alcohol), butanol and isobutyl alcohol; glycols such as propylene glycol, 1,3-butylene glycol, diethylene glycol, dipropylene glycol, and isopentyl diol.

Other solvents 112 may include, without limitation: glycol ethers, such as ethylene glycol monoethyl ether (ethoxydiglycol), ethylene glycol monoethyl ether, ethylene glycol butyl ether, triethylene glycol monoethyl ether, diethylene glycol diethyl ether, diethylene glycol dibutyl ether, propylene glycol monoethyl ether, dipropylene glycol monoethyl ether; Glycol ether esters such as ethylene glycol monoethyl ether acetate, diethylene glycol monoethyl ether acetate, propylene glycol monoethyl ether acetate, glycol ether esters such as diethoxyethyl succinate, ethylene glycol disuccinate; benzyl alcohol, benzyloxyethanol, propylene carbonate, dialkyl carbonate, acetone, ethyl acetate, N-methyl pyrrolidone; toluene, fluorocarbon, next generation freon; LPG, dimethyl ether, carbon dioxide, cellosolve, dioxane, dimethylformamide, dimethyl sulfoxide, and crotamiton.

The Tables in FIGS. 2A-6 further illustrate various combinations of ingredients that make up different embodiments of the compositions, and the evaluation and results derived from use of the composition 100. The ingredients for the first and second agent variations of the composition 100 may be identified by chemical or CTFA name. The composition 100 and mixing of the ingredients can be prepared by any conventional means known in the art.

Looking now at the Table in FIG. 2A, one possible embodiment of the ingredients used in an exemplary composition 200 include the following: a polyoxyethylene tridecyl ether having an HLB of 8.3, 11.4, and 14.5; and comprising 10% by total weight of composition. The polyoxyethylene tridecyl ether can be the nonionic surfactant 102 discussed above. Further, this embodiment of the composition 200 includes a lauryl alcohol comprising 6% by total weight of composition. This embodiment further includes a myristal alcohol comprising 4% by total weight of composition. This embodiment further includes a sodium c14-16 olefin sulfonate comprising 7% by total weight of composition. This embodiment of the composition 200 further includes an isopropyl alcohol comprising 10% by total weight of the composition.

A dye is also used in this embodiment of the composition 200, which includes toluene-2,5-diamine and 2,4-diaminophenoxyethanol HCl, both comprising 0.2% by total weight of the composition. The alkaline agent used in the present embodiment is ethanolamine comprising 2% by total weight of composition. The composition 200 also utilizes an antioxidant, such as sodium sulfite, that is 0.3% by total weight of the composition. The composition 200 also utilizes a chelating agent, such as pentasodium pentetate, that is 0.1% by total weight of the composition. The solvent used in this embodiment of the composition 200 is water that can have up to 100% total weight of the composition.

In evaluating the feel of the hair after application of the composition 200, a feel test, shown in the Table 202 of FIG. 2B, displays hair softness evaluation criteria in the ranges of 26-30; 20-25; and 19 or less, with 30 characterizing the softest feel of the hair, and 19 characterizing an undesirable feel of hair, such as dried hair cuticles, split ends, and the like. The composition 200, once applied to the hair, achieves the 26-30 range of softness.

Further, the stability criteria of the composition 200 is also documented in the Table 204 shown in FIG. 2C. It is significant to note that when stable, the composition 200 prevents drooping down of the hair during application and during standing of the composition 200. It is thus, necessary to provide a hair dying and conditioning composition that is stable over time. The stability helps overcome adverse effects of dying hair, such as roughness of the hair cuticle, and the undesirable/rough feel of the hair to finish is reduced to a lesser degree. The evaluation criteria of stability includes: No Separation and Precipitation; and Separation and Precipitation. As shown in the Table, the composition 200 proves to be extremely stable by exhibiting Separation and Precipitation.

Looking now at the Table in FIG. 3, a second embodiment of an exemplary composition 300 includes the following ingredients: a polyoxyethylene tridecyl ether trideceth-6 comprising 10% by total weight of composition. The polyoxyethylene tridecyl ether trideceth-6 can be the nonionic surfactant 102 discussed above. Further, this embodiment of the composition 300 includes a lauryl alcohol having an N of C of 12, and comprising 4% or 6% by total weight of composition. This embodiment further includes a myristal alcohol having an N of C of 14, and comprising 4% by total weight of composition. Further, this embodiment of the composition 300 includes an oleyl alcohol having an N of C of 16, and comprising 4% by total weight of composition. This embodiment further includes a sodium C14-16 olefin sulfonate comprising 7% by total weight of composition. This embodiment of the composition 300 further includes an isopropyl alcohol comprising 10% by total weight of the composition.

A dye is also used in this embodiment of the composition 300, which includes toluene-2,5-diamine and 2,4-diaminophenoxyethanol HCl, both comprising 0.2% by total weight of the composition. The alkaline agent used in the present embodiment is ethanolamine comprising 2% by total weight of composition. The composition 300 also utilizes an antioxidant, such as sodium sulfite, that is 0.3% by total weight of the composition. The composition 300 also utilizes a chelating agent, such as pentasodium pentetate, that is 0.1% by total weight of the composition. The solvent used in this embodiment of the composition 300 is water that can have up to 100% total weight of the composition.

A third possible embodiment of the composition is referenced in Table in FIG. 4. An exemplary composition 400 includes the following ingredients: a polyoxyethylene tridecyl ether trideceth-6 comprising 10% by total weight of composition. The polyoxyethylene tridecyl ether trideceth-6 can be the nonionic surfactant 102 discussed above. Further, this embodiment of the composition 400 includes a lauryl alcohol comprising 4% by total weight of composition. This embodiment further includes a myristal alcohol comprising 4% by total weight of composition. Further, this embodiment of the composition 400 includes a sodium C14-16 olefin sulfonate having an anionic SAA and comprising 3.5% and 7% by total weight of composition. Further, this embodiment of the composition 400 includes a coco betaine having an amphoteric SAA and comprising 3.5% and 7% by total weight of composition. This embodiment further includes an isopropyl alcohol comprising 10% by total weight of the composition.

In this embodiment, the dyes is used in the composition 400 are toluene-2,5-diamine and 2,4-diaminophenoxyethanol HCl, both comprising 0.2% by total weight of the composition. The alkaline agent used in the present embodiment is ethanolamine comprising 2% by total weight of composition. The composition 400 also utilizes an antioxidant, such as sodium sulfite, that is 0.3% by total weight of the composition. The composition 400 also utilizes a chelating agent, such as pentasodium pentetate, that is 0.1% by total weight of the composition. The solvent used in this embodiment of the composition 400 is water that can have up to 100% total weight of the composition.

The Table in FIG. 5 references a fourth possible embodiment of an exemplary composition 500. In this embodiment, the composition 500 includes a polyoxyethylene tridecyl ether trideceth-6 comprising 10% by total weight of composition. The polyoxyethylene tridecyl ether trideceth-6 can be the nonionic surfactant 102 discussed above. Further, this embodiment of the composition 500 includes a lauryl alcohol comprising 4% by total weight of composition. This embodiment further includes a myristal alcohol comprising 4% by total weight of composition. Further, this embodiment of the composition 500 includes a sodium C14-16 olefin sulfonate having an anionic SAA and comprising 3.5% and 7% by total weight of composition. Further, this embodiment of the composition 500 includes a coco betaine having an amphoteric SAA and comprising 3.5% and 7% by total weight of composition. This embodiment further includes an isopropyl alcohol comprising 10% by total weight of the composition.

In this embodiment, the dyes is used in the composition 500 are toluene-2,5-diamine and 2,4-diaminophenoxyethanol HCl, both comprising 0.2% by total weight of the composition. The alkaline agent used in the present embodiment is ethanolamine comprising 2% by total weight of composition. The composition 500 also utilizes an antioxidant, such as sodium sulfite, that is 0.3% by total weight of the composition. The composition 500 also utilizes a chelating agent, such as pentasodium pentetate, that is 0.1% by total weight of the composition. The solvent used in this embodiment of the composition 500 is water that can have up to 100% total weight of the composition.

FIG. 6 references a Table listing the ingredients for a fifth possible embodiment of an exemplary composition 600. The ingredients include a polyoxyethylene tridecyl ether trideceth-6 comprising 10% by total weight of composition. The polyoxyethylene tridecyl ether trideceth-6 can be the nonionic surfactant 102 discussed above. Further, this embodiment of the composition 600 includes a lauryl alcohol comprising 6% by total weight of composition. This embodiment further includes a myristal alcohol comprising 4% by total weight of composition. Further, this embodiment of the composition 600 includes a sodium C14-16 olefin sulfonate having an anionic SAA and comprising 7% by total weight of composition.

This embodiment further includes examples of the composition 600 consisting of an isopropyl alcohol comprising 3.5%, 7%, and 10% by total weight of the composition. In this embodiment, the dyes is used in the composition 600 are toluene-2,5-diamine and 2,4-diaminophenoxyethanol HCl, both comprising 0.2% by total weight of the composition. The alkaline agent used in the present embodiment is ethanolamine comprising 2% by total weight of composition. The composition 600 also utilizes an antioxidant, such as sodium sulfite, that is 0.3% by total weight of the composition. The composition 600 also utilizes a chelating agent, such as pentasodium pentetate, that is 0.1% by total weight of the composition. The solvent used in this embodiment of the composition 600 is water that can have up to 100% total weight of the composition. As the Table shows, for this fifth embodiment of the composition 600, the feel test is characterizes as 27; and the stability is characterized as semi-solid.

Looking back at FIG. 1, the composition 100 may include an oxidative hair dye kit 113 that facilitates the process of base breaking the hair, i.e., reducing the contrast between a hair's natural base color and highlights. The kit 113 comprises variants of the composition 100 in a first agent 114*a* and a second agent 114*b* that are applied in phases on the section of hair requiring base breaking. In one non-limiting embodiment, the first agent 114*a* consists of an oxidative dye and an alkaline agent, and the second agent 114*b* consists of an oxidative agent. The two agents 114*a*, 114*b* are applied in different two phases separated by a duration of at least ten minutes between applications, and washing and drying of the hair.

In some embodiments, the first agent 114*a* for oxidation dyeing of the hair may include, without limitation, an oxidation dye, an alkaline agent, an oil component, a surfactant, and a solvent. The second agent 114*b* may include only an oxidizing agent. However in other embodiments, the second agent 114*b* may include the oxidizing agent in addition to the ingredients found in the first agent 114*a*. In one non-limiting embodiment, the kit 113 is configured so that the first and second agent 114*bs* are contained in separate containers to facilitate application to the hair in different phases.

In addition to the above-mentioned components, the first agent 114*a* for oxidation hair dye composition 100 may further contain a solvent, an oil component other than that mentioned above, a direct dye, a stabilizer for an oxidation dye, a stabilizer in an emulsified state, a pH regulator, an animal and plant extract, water soluble polymer, amino acid and its derivatives, protein and its derivatives, vitamin agent, ultraviolet protective agent, antioxidant, sequestering agent, and a fragrance.

The oxidation dye used in the first agent 114*a* may further include a dye intermediate that helps develops color by polymerization alone, or a combination of the coupler with a dye intermediate that develops color upon polymerization in combination with a coupler. The dye intermediate is not particularly limited as long as it can be blended in the first agent 114*a* for oxidation hair dyeing. Examples of the dye intermediate include: toluene-2,5-diamine hydrochloride, paraphenylenediamine hydrochloride, o-aminophenol, p-aminophenol, toluene-2,5-diamine, toluene-3,4-diamine, p-aminophenol, p-methylaminophenol, orthoaminophenol sulfate, orthochloroparaphenylenediamine sulfate, 4, 4'-diaminodiphenylamine sulfate, toluene-2,5-diamine sulfate, p-methylaminophenol sulfate, paraphenylene diamine sulfate and paramethylaminophenol sulfate etc., Further, as necessary couplers to be combined with the dye intermediate, for example, 2,4-diaminophenoxyethanol hydrochloride, m-phenylenediamine, 2,6-diaminopyridine, 5-aminoorthocresol, m-aminophenol, α-naphthol, hydroquinone, resorcinol, catechol, 3,3'-iminodiphenol, 2,4-diaminophenol hydrochloride, metaphenylene diamine hydrochloride, 1,5-dihydroxynaphthalene, 5-(2-hydroxyethylamino)-2-methylphenol, 5-aminoorthocresol sulfate, 2,4-diaminophenol sulfate, metaaminophenol sulfate, and meta-phenylenediamine sulfate. From the viewpoint of safety, it is preferable not to include only paraphenylene diamine.

The stabilizer used in the first agent 114*a* of the composition 100 may include, without limitation: ascorbic acids, thioglycolic acids, cysteines, mercapto compounds, sulfites, bisulfites, thiosulfates and the like. The pH adjuster used in the first agent 114*a* of the composition 100 may include, without limitation: acids such as citric acid, phosphoric acid, malic acid, tartaric acid, and lactic acid; and salts such as sodium citrate and disodium phosphate.

In addition to the above-mentioned components, the first agent 114*a* may contain a solvent, at least one liquid oil agent 104 and at least one C14 or higher alcohol, direct dyes, stabilizers for oxidation dyes, stabilizers in emulsified state, pH adjusters, animal and plant extracts, water-soluble polymers, amino acids and derivatives thereof, proteins and derivatives thereof, vitamins, UV protective agent, antioxidants, a sequestering agent and perfume etc. These ingredients may be blended into the first agent 114*a* for enhancing the oxidation of the hair while dyeing. Further, the first agent 114*a* can be configured more uniformly and darkly to further reduce adverse effects on the feel of the hair, so that it is particularly suitable for hair dyeing uneven colored hairs including white hair.

FIG. 7 illustrates a flowchart of an exemplary method 700 for base breaking hair with an oxidative hair dye composition. The method 700 is effective for removing a hair border line that often occurs in the hair dying process. The method 700 includes steps for reducing the contrast between a hair's natural base color and highlights.

For purposes of this invention, base breaking is defined as a technique for wiping out the boundary line between upper portion and root portions of the hair through use of a new hair and a bright hair. This is expressed as a numerical pattern in a short time and with low damping effect on the hair—even in the case of fading. Since the variation between the touch and boundary lines are not clear, and there is little damage to the hair, the method 700 of base breaking the hair, as taught here, provides numerous advantageous.

In one non-limiting embodiment illustrated in a base breaking process 800 of FIGS. 8A-8E, a first agent 114*a* consisting of an oxidative dye and alkaline agent; and a second agent 114*b* consisting of an oxidative agent are applied to the hair in two different phases separated by a duration of at least ten minutes, and rinsing/drying of the hair between applications. In some embodiments, the first agent 114*a* for oxidation dyeing may include an oxidation dye, an alkaline agent, an oil component, a surfactant, and a solvent.

In some embodiments, the second agent 114*b* may include only an oxidizing agent. However in other embodiments, the second agent 114*b* may include the oxidizing agent in addition to the ingredients found in the first agent 114*a*. The kit 113 is configured so that the first and second agents 114*a*, 114*b* are contained in separate containers to facilitate application to the hair in different phases.

Figure 8A:
FIGS. 8A-8E are perspective views of the method base breaking the hair, where

In some embodiments, the method 700 may include an initial Step 702 of parting the hair to expose a contrast between a hair's natural base color and highlights. FIG. 8A shows the hair parted in preparation for base breaking. The variations in color are clearly shown when the hair is parted to reveal the root portion of the hair follicle. In one non-limiting embodiment of the method 700, the base breaking process 800 is performed on a set surface or on a shampoo stand, such that the set surface separates the new hair and the pre-bleached hair.

Figure 8B:

As FIG. 8B illustrates, the method 700 further includes a Step 704 of applying a first agent 114*a* to the contrasting area of the hair, the first agent 114*a* consisting of an oxidative dye and alkaline agent, whereby the first agent 114*a* stains the hair. In some embodiments, the first agent 114*a* for oxidation dyeing of the hair may include, without limitation, an oxidation dye, an alkaline agent, an oil component, a surfactant, and a solvent. In some embodiments, the oxidative hair dye composition 100 to be applied has a viscosity that can be applied to the new hair and the pre-existing hair.

The first agent 114*a* for oxidation hair dye composition 100 may further contain a solvent, an oil component other than that mentioned above, a direct dye, a stabilizer for an oxidation dye, a stabilizer in an emulsified state, a pH regulator, an animal and plant extract, water soluble polymer, amino acid and its derivatives, protein and its derivatives, vitamin agent, ultraviolet protective agent, antioxidant, sequestering agent, and a fragrance.

The oxidation dye used in the first agent 114*a* may further include a dye intermediate that helps develops color by polymerization alone, or a combination of the coupler with a dye intermediate that develops color upon polymerization in combination with a coupler. The dye intermediate is not particularly limited as long as it can be blended in the first agent 114*a* for oxidation hair dyeing.

Examples of the dye intermediate include: toluene-2,5-diamine hydrochloride, paraphenylenediamine hydrochloride, o-aminophenol, p-aminophenol, toluene-2,5-diamine, toluene-3,4-diamine, p-aminophenol, p-methylaminophenol, orthoaminophenol sulfate, orthochloroparaphenylenediamine sulfate, 4, 4'-diaminodiphenylamine sulfate, toluene-2,5-diamine sulfate, p-methylaminophenol sulfate, paraphenylene diamine sulfate and paramethylaminophenol sulfate etc., Further, as necessary couplers to be combined with the dye intermediate, for example, 2,4-diaminophenoxyethanol hydrochloride, m-phenylenediamine, 2,6-diaminopyridine, 5-aminoorthocresol, m-aminophenol, α-naphthol, hydroquinone, resorcinol, catechol, 3,3'-iminodiphenol, 2,4-diaminophenol hydrochloride, metaphenylene diamine hydrochloride, 1,5-dihydroxynaphthalene, 5-(2-hydroxyethylamino)-2-methylphenol, 5-aminoorthocresol sulfate, 2,4-diaminophenol sulfate, metaaminophenol sulfate, and meta-phenylenediamine sulfate. From the viewpoint of safety, it is preferable not to include only paraphenylene diamine.

The stabilizer used in the first agent 114*a* of the composition may include, without limitation: ascorbic acids, thioglycolic acids, cysteines, mercapto compounds, sulfites, bisulfites, thiosulfates and the like. The pH adjuster used in the first agent 114*a* of the composition may include, without limitation: acids such as citric acid, phosphoric acid, malic acid, tartaric acid, and lactic acid; and salts such as sodium citrate and disodium phosphate.

In addition to the above-mentioned components, the first agent 114*a* may contain a solvent, at least one liquid oil agent and at least one C14 or higher alcohol, direct dyes, stabilizers for oxidation dyes, stabilizers in emulsified state, pH adjusters, animal and plant extracts, water-soluble polymers, amino acids and derivatives thereof, proteins and derivatives thereof, vitamins, UV protective agent, antioxidants, a sequestering agent and perfume etc.

These ingredients may be blended into the first agent 114*a* for enhancing the oxidation of the hair while dyeing. Further, the first agent 114*a* can be configured more uniformly and darkly to further reduce adverse effects on the feel of the hair, so that it is particularly suitable for hair dyeing uneven colored hairs including white hair. The Tables in FIGS. 2A-6 further illustrate various combinations of ingredients and the evaluation and results derived from use of the first and second agent derivations of the oxidative hair dye composition used in the method 700. The ingredients for the first and second agents are identified by chemical or CTFA name.

Figure 8C:
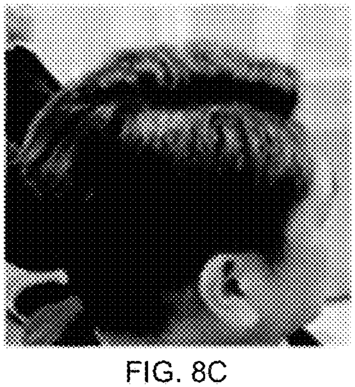

In some embodiments, a Step 706 includes waiting for a duration of at least ten minutes. In general, de-colorization is sufficient for 10 minutes after application, whereas coloration is insufficient for 10 minutes, requiring a greater duration and having the following coloration scheme: blue→green→yellow→orange→red→purple. It may be preferable to use a color that produces a blue color and does not produce a red color because it is colored in the order. Step 708 comprises rinsing the hair. In rinsing, the stained section of the hair is primarily flushed with water to remove excess first agent 114*a*, dyes, and loose hair follicles. A Step 710 includes drying the hair. A towel or air dryer may be used to dry the hair in preparation for application of the second agent 114*b*. FIG. 8C shows the hair after the first application and the rinsing and drying steps are complete.

Figure 8D:
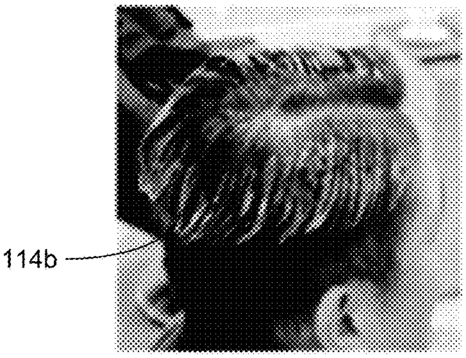

Looking now at FIG. 8D, a Step 712 may include applying a second agent 114*b* to the stained hair, the second agent 114*b* consisting of an oxidative agent. The second agent 114*b* may include only the oxidative agent; or the oxidative agent and any of the ingredients listed above for the first agent 114*a*. For example, the second agent 114*b* may include, without limitation, an oxidation dye, an alkaline agent, an oil component, a surfactant, a solvent, a stabilizer, and a dye intermediate that helps develops color by polymerization alone.

Further, the mode of application of the first and second agents 114*a*, 114*b* is not limited, as long as the first agent 114*a* and the second agent 114*b* are at one point of the process combined in a mixed state on the hair. For example, the first agent 114*a* and the second agent 114*b* can be mixed and then applied to the hair; or the first agent 114*a* can be applied to the hair alone; or the second agent 114*b* can be applied to the hair alone. In yet another embodiment, the second agent 114*b* containing the oxidizing agent may be mixed with the first agent 114*a* and the second agent 114*b* at the time of use. Other combinations and application means known in the art may also be used.

The method 700 may further include a Step 714 of waiting for a duration of at least ten minutes. The duration of ten minutes is approximate; and may be longer or shorter, depending on the difference in coloration between the highlighted section of the hair and the root portion. A Step 716 comprises re-rinsing the hair. Here, the hair rinsing process is similar to the first rinse. The first and second agent 114*bs* are substantially removed during rinsing.

A final Step 718 includes re-drying the hair. The results are shown in block diagram of FIG. 9, which references the hair follicle after treatment for a duration of 10 minutes and two months, shown with two very different shades of hair coloring. The hair follicle 900 is shown with two very different shades of hair coloring. A root portion 902 of the hair follicle is dark, while an upper portion 904 of the hair follicle—the highlighted portion—is light colored. After applying the first agent 114*a*, and waiting the ten minute duration, the upper portion 904 of the hair follicle changes to a darker shade that is closer to the root portion 902 of the hair follicle 900. After two months of treatment, there is clearly less variation of color differences, as the hair follicle 900 has been stained with three slightly varying colors.

Figure 10:
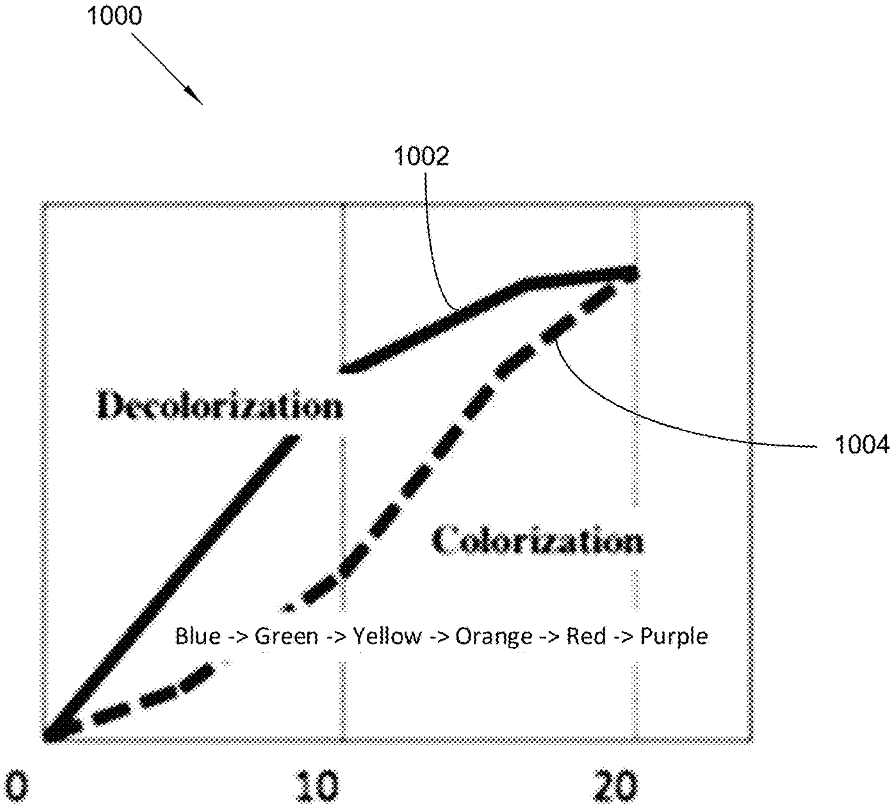
FIG. 10 illustrates a graph showing the effects of color enhancement after a duration of 0 minutes, 10 minutes, and 20 minutes for both colorization and de-colorization treatments, in accordance with an embodiment of the present invention.

FIG. 10 illustrates a graph 1000 showing the effects of color enhancement after a duration of 0 minutes, 10 minutes, and 20 minutes for both colorization and de-colorization treatments. A de-colorization line 1002 (de-colorization treatment) shows that 10 minutes of wait time is sufficient after application, whereas a coloration line 1004 (colorization treatment) shows that a 10 minute waiting time is insufficient; thereby requiring a greater duration of waiting.

As the graph 1000 shows, the colorization line 1004 includes the following coloration scheme: blue→green→yellow→orange→red→purple. Though it is preferable to use a color that produces a blue color and does not produce a red color because it is colored in the order. Those skilled in the art will recognize that it is possible to express the numerical charts in a short time with a low degree of damping by using dark new hair and bright hair. Even at the time of fading, the conventional retouching and boundary line are not clear and there is a considerable margin because there are fewer damages.

Figure 8E:
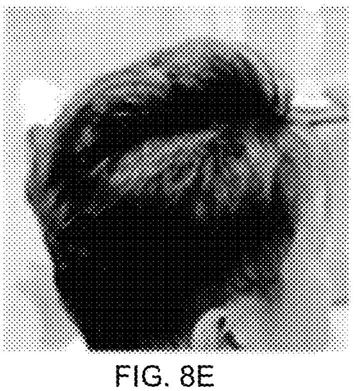
Figure 9:
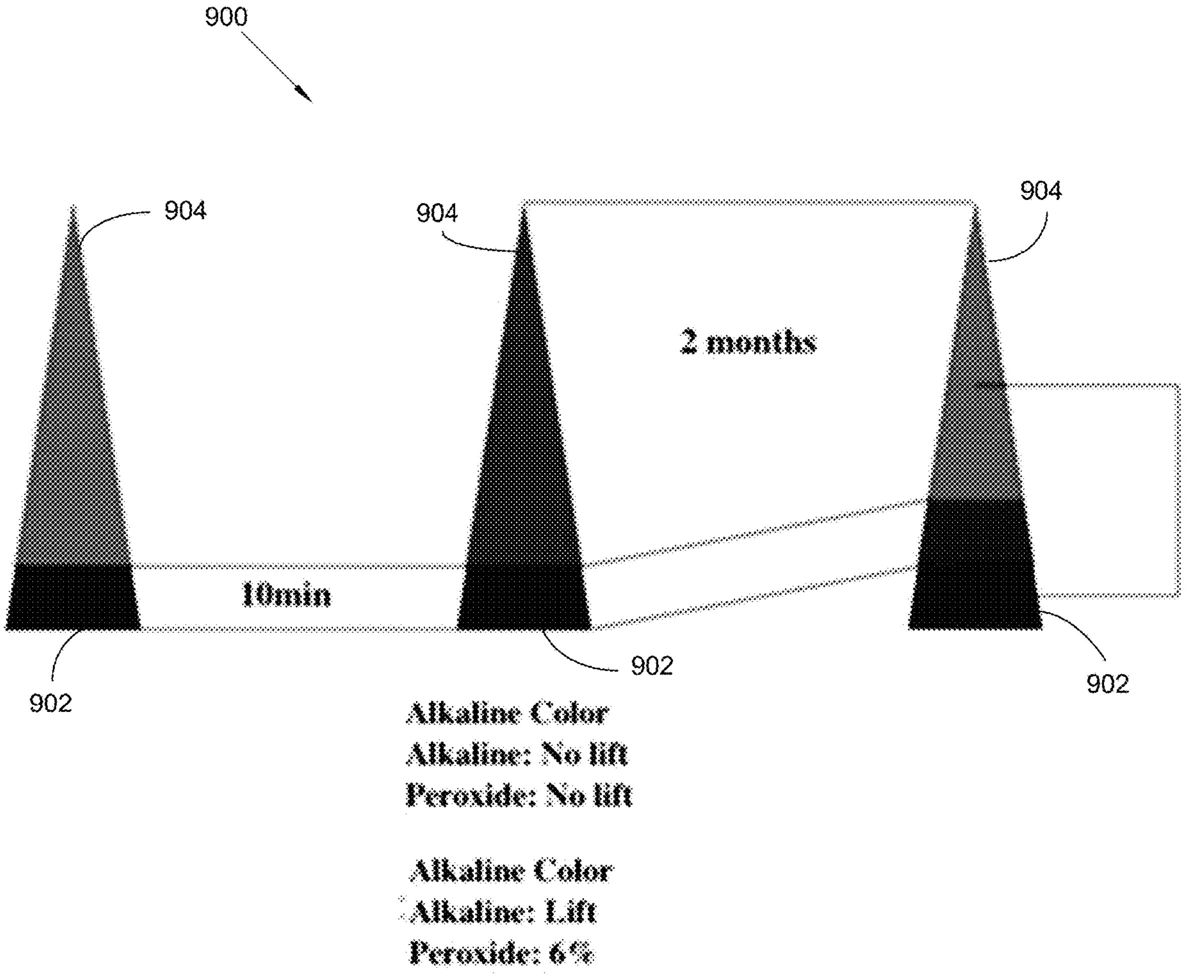
FIG. 9 illustrates a block diagram showing the hair follicle after treatment for a duration of 10 minutes and two months, shown with two very different shades of hair coloring, in accordance with an embodiment of the present invention.

It is significant to note that when discoloration occurs, the difference between new unmolested hair, hair dyed with the first agent, and hair dyed with both the first and second agent is small because the composition does not have the ability to lift dyes from the hair follicle (see FIG. 8E). It is also significant to note that for users who have had a haircut once, the newborn section of hair, color development, and de-colorization are performed simultaneously for 10 minutes with the hair color of blue color center. This creates a lifting force, and color development, possible through use of an aliquot.

Although the process-flow diagrams show a specific order of executing the process steps, the order of executing the steps may be changed relative to the order shown in certain embodiments. Also, two or more blocks shown in succession may be executed concurrently or with partial concurrence in some embodiments. Certain steps may also be omitted from the process-flow diagrams for the sake of brevity. In some embodiments, some or all the process steps shown in the process-flow diagrams can be combined into a single process.

While the specification concludes with claims particularly pointing out and distinctly claiming the invention, it is believed that the present invention will be better understood from the following description. All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A method for base breaking hair with an oxidative hair dye composition, the method comprising:

parting the hair to expose a contrast between a hair's natural base color and highlights;

applying the oxidative hair dye composition comprising a first agent to the contrasting area of the hair; wherein the first agent comprises a dye intermediate, a nonionic surfactant having a hydrophilic-lipophilic balance of 12 or less, being present in an amount of from about 12% to about 18% by weight, based on the total weight of the oxidative hair dye composition, at least one liquid oil agent being present in an amount of from 7.5% to 11.5% by weight, based on the total weight of the oxidative hair dye composition, at least one alcohol defined by a carbon chain of at least 14 carbon atoms being present in an amount of from about 0.01% to 3% by weight, based on the total weight of the oxidative hair dye composition, at least one anion surfactant being present in an amount of from about 6% to 9% by weight, based on the total weight of the oxidative hair dye composition, at least one amphoteric surfactant being present in an amount of from about 6% to 9% by weight, based on the total weight of the oxidative hair dye composition, at least one solvent being present in an amount of from about 10% to 20% by weight, based on the total weight of the oxidative hair dye composition;

applying the oxidative hair dye composition comprising a second agent mixing with the first agent to the stained hair, wherein the second agent comprises hydrogen peroxide;

waiting for at least ten minutes;

rinsing the hair;

drying the hair;

applying the oxidative hair dye composition having the second agent mixing with the first agent to the stained hair;

re-rinsing the hair; and re-drying the hair.

2. The method of claim 1, wherein the dye intermediate being selected from a group consisting of toluene-2,5-diamine hydrochloride, paraphenylenediamine hydrochloride, o-aminophenol, p-aminophenol, toluene-2,5-diamine, toluene-3,4-diamine, p aminophenol, p-methylaminophenol, orthoaminophenol sulfate, orthochloroparaphenylenediamine sulfate, 4,4'-diaminodiphenylamine sulfate, toluene-2,5-diamine sulfate, p-methylaminophenol sulfate, paraphenylene diamine sulfate and paramethylaminophenol sulfate.

3. The method of claim 1, wherein the first agent further comprises a stabilizer being selected from a group consisting of ascorbic acids, thioglycolic acids, cysteines, mercapto compounds, sulfites, bisulfites, and thiosulfates.

4. The method of claim 2, wherein the first agent further comprises couplers to be combined with the dye intermediate, wherein the couplers are selected from a group consisted of 2,4-diaminophenoxyethanol hydrochloride, m-phenylenediamine, 2,6-diaminopyridine, 5-aminoorthocresol, m-aminophenol, a-naphthol, hydroquinone, resorcinol, catechol, 3,3'-iminodiphenol, 2,4-diaminophenol hydrochloride, metaphenylene diamine hydrochloride, 1,5-dihydroxynaphthalene, 5-(2-hydroxyethylamino)-2-methylphenol, 5-aminoorthocresol sulfate, 2,4-diaminophenol sulfate, metaaminophenol sulfate, and metaphenylenediamine sulfate.

* * * * *